(12) United States Patent
Bainbridge et al.

(10) Patent No.: US 11,351,523 B2
(45) Date of Patent: Jun. 7, 2022

(54) PROCESS FOR REGENERATING A DEACTIVATED VANADIUM-TITANIUM-PHOSPHOROUS CATALYST

(71) Applicant: JOHNSON MATTHEY DAVY TECHNOLOGIES LIMITED, London (GB)

(72) Inventors: Michael Bainbridge, Durham (GB); Javad Tabatabaei, Durham (GB)

(73) Assignee: Johnson Matthey Davy Technologies Limited, London (GB)

( * ) Notice: Subject to any disclaimer, the term of this patent is extended or adjusted under 35 U.S.C. 154(b) by 234 days.

(21) Appl. No.: 16/334,780

(22) PCT Filed: Sep. 21, 2017

(86) PCT No.: PCT/GB2017/052826
§ 371 (c)(1),
(2) Date: Mar. 20, 2019

(87) PCT Pub. No.: WO2018/055383
PCT Pub. Date: Mar. 29, 2018

(65) Prior Publication Data
US 2019/0232259 A1    Aug. 1, 2019

(30) Foreign Application Priority Data
Sep. 22, 2016  (GB) .................................... 1616119

(51) Int. Cl.
*B01J 27/28*       (2006.01)
*B01J 38/02*       (2006.01)
(Continued)

(52) U.S. Cl.
CPC .......... *B01J 27/285* (2013.01); *B01J 27/198* (2013.01); *B01J 38/02* (2013.01); *B01J 38/06* (2013.01);
(Continued)

(58) Field of Classification Search
CPC ........ B01J 27/285; B01J 27/198; B01J 35/02; B01J 38/06; B01J 38/12; B01J 38/16;
(Continued)

(56) References Cited

U.S. PATENT DOCUMENTS 2,773,921 A * 12/1956 Rylander, Jr. ............. C07C 2/18
585/466
3,358,020 A * 12/1967 Hendrickx ............... C07C 53/08
562/534
(Continued)

FOREIGN PATENT DOCUMENTS

CN   101554593     * 10/2009 ............. B01J 31/18
CN   101554593 A    10/2009
(Continued)

OTHER PUBLICATIONS

Mamoru Ai, Vapor-Phase Aldol Condensation of Formaldehyde With Acetic Acid on V2O5—P2O5 Catalysts, Journal of Catalysis 107, 201-208, 1987.
(Continued)

*Primary Examiner* — Patricia L. Hailey
(74) *Attorney, Agent, or Firm* — BakerHostetler

(57) ABSTRACT

A process for regenerating a deactivated vanadium-titanium-phosphorous catalyst which has been used in the production of unsaturated carboxylic acid is disclosed. The process comprises contacting the deactivated vanadium-titanium-phosphorous catalyst with a regeneration stream comprising
(Continued)

Figure 1:
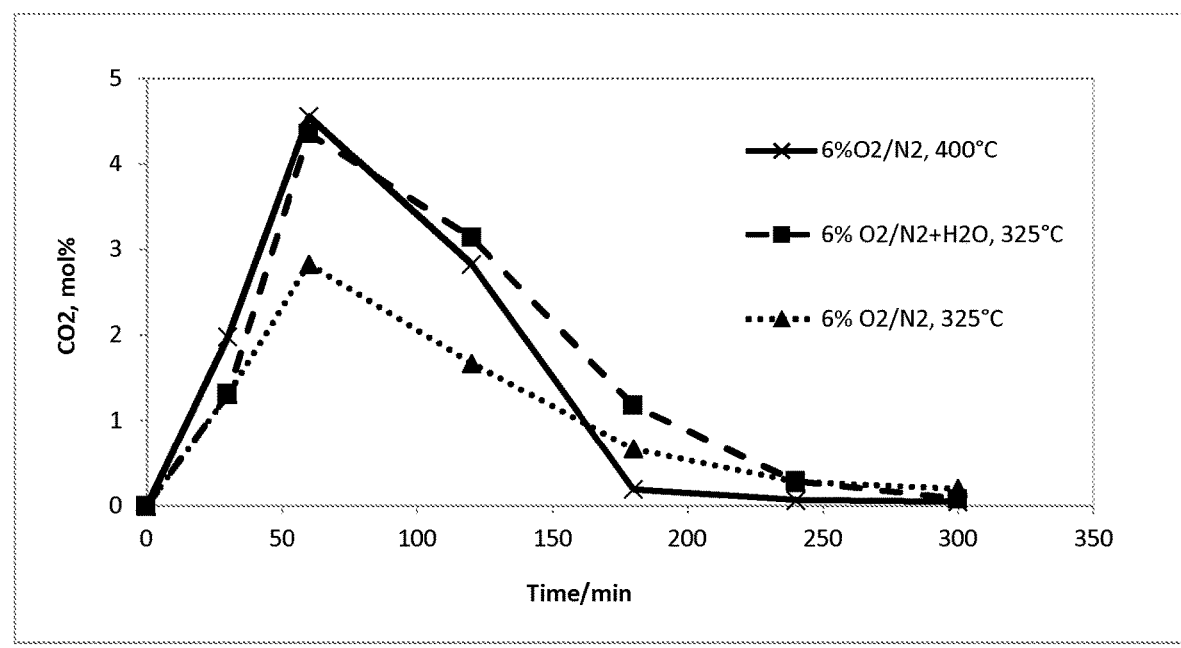

steam as a regeneration agent at a temperature which is the same or similar to that used in the production of the unsaturated carboxylic acid.

10 Claims, 2 Drawing Sheets

(51) Int. Cl.
  *B01J 38/06* (2006.01)
  *B01J 38/16* (2006.01)
  *B01J 27/198* (2006.01)
  *C07C 51/353* (2006.01)
(52) U.S. Cl.
  CPC ............. *B01J 38/16* (2013.01); *C07C 51/353* (2013.01); *Y02P 20/584* (2015.11)
(58) Field of Classification Search
  CPC ....... B01J 23/22; B01J 21/063; C07C 51/353; Y02P 20/584
  USPC ....... 502/34, 38, 51, 55, 209, 312, 350, 353; 562/509
  See application file for complete search history.

(56) References Cited

U.S. PATENT DOCUMENTS

| | | | |
|---|---|---|---|
| 4,276,197 A | | 1/1981 | Vartuli et al. |
| 4,447,638 A | * | 5/1984 | Gaffney .................. C07C 67/36 560/204 |
| 4,515,899 A | * | 5/1985 | Click ...................... B01J 27/285 502/209 |
| 4,861,738 A | * | 8/1989 | Edwards ................ B01J 23/002 502/34 |
| 5,474,960 A | * | 12/1995 | Bremer .................. B01J 27/285 422/149 |
| 5,521,134 A | * | 5/1996 | Bortinger ................ B01J 23/92 502/209 |
| 5,710,328 A | * | 1/1998 | Spivey ................... B01J 23/002 562/599 |
| 5,854,161 A | * | 12/1998 | Ichiki ...................... B01J 38/00 502/41 |
| 6,664,206 B2 | * | 12/2003 | Kasuga .................. C07C 57/04 502/208 |
| 8,642,498 B2 | | 2/2014 | Nagaki et al. |
| 8,652,988 B2 | | 2/2014 | Nagaki et al. |
| 8,652,989 B2 | | 2/2014 | Sato et al. |
| 8,658,822 B2 | | 2/2014 | Mueller et al. |
| 8,735,314 B2 | | 5/2014 | Nagaki et al. |
| 8,765,629 B2 | | 7/2014 | Norman et al. |
| 8,802,585 B2 | * | 8/2014 | Weiner .................... B01J 23/22 502/150 |
| 8,877,966 B2 | | 11/2014 | Herzog et al. |
| 8,889,586 B2 | | 11/2014 | Nagaki et al. |
| 9,573,119 B2 | * | 2/2017 | Deng ..................... B01J 37/031 |
| 2007/0179042 A1 | | 8/2007 | Pessoa Cavalcanti et al. |
| 2007/0185339 A1 | * | 8/2007 | Lu ............................ B01J 23/50 549/534 |
| 2012/0071688 A1 | | 3/2012 | Herzog et al. |
| 2012/0149549 A1 | | 6/2012 | Boeing et al. |
| 2014/0121410 A1 | * | 5/2014 | Mueller ................ C07C 51/353 562/599 |
| 2014/0277384 A1 | | 9/2014 | Melsheimer |
| 2014/0343318 A1 | | 11/2014 | Gruene et al. |
| 2014/0343319 A1 | | 11/2014 | Goebel et al. |

FOREIGN PATENT DOCUMENTS

| | | | |
|---|---|---|---|
| EP | 0384755 A1 | 8/1990 | |
| WO | WO 96/32193 | * 10/1996 | ............... B01J 23/92 |

OTHER PUBLICATIONS

GB1715259.6 Combined Search and Examination Report dated Mar. 15, 2018.
GB1616119.2 Search Report Under Section 17(5) dated Mar. 23, 2017.
PCT/GB2017/052826 International Search Report dated Dec. 6, 2017.
PCT/GB2017/052826 Written Opinion dated Dec. 6, 2017.

* cited by examiner

PROCESS FOR REGENERATING A DEACTIVATED VANADIUM-TITANIUM-PHOSPHOROUS CATALYST

CROSS-REFERENCE TO RELATED APPLICATIONS

This application is the National Stage of International Patent Application No. PCT/GB2017/052826, filed Sep. 21, 2017, which claims priority from Great Britain Patent Application No. 1616119.2, filed Sep. 22, 2016, the entire disclosures of each of which applications are incorporated herein by reference for any and all purposes.

The present invention relates to a process for regenerating vanadium-titanium-phosphorous catalysts. More particularly, it relates to a process for regenerating catalysts which have been used in the production of unsaturated carboxylic acids, such as acrylic acid.

Conventional commercial processes for the production of acrylic acid have relied on the gas phase oxidation of propylene, via acrolein, to form acrylic acid. Whilst the process may be effective, the oxidation reaction is highly exothermic and therefore creates an explosion risk. To minimise the risk, more expensive reactor designs and more expensive metallurgy are required. In addition, the cost of the propylene starting material is generally high which adversely affects the economics of the process. In addition, the supply of the propylene can be insecure and limited.

Alternative routes to acrylic acid have therefore been investigated. One route which has gained interest is the aldol condensation reaction of formaldehyde with acetic acid. This aldol condensation, which takes place over a vanadium oxide-phosphorus oxide catalyst, has been described in Mamoru Ai, Vapor-Phase Aldol Condensation of Formaldehyde with Acetic Acid on $V_2O_5$—$P_2O_5$ Catalysts, Journal of Catalysis 107, 201-208, 1987. The main benefit of the route is it moves the use of feedstock for acrylic acid away from propylene to other sources of carbon.

One example of a process for producing acrylic acids and acrylates by reacting formaldehyde and acetic acid is described in U.S. Pat. No. 8,658,822. In the process described in U.S. Pat. No. 8,658,822, the alkylenating agent, namely formaldehyde, is used in excess relative to the stoichiometric amount of alkanoic acid, namely acetic acid. In particular, a formaldehyde to acetic acid molar ratio of between 1 and 10, and preferably between 1.16 and 1.9 is described. A stoichiometric excess of alkanoic acid relative to alkylenating agent is suggested to be desired in order to improve acrylate selectivity. The process described may optionally also include water, oxygen, and methanol.

Various catalysts have been investigated in relation to their use in aldol condensation reactions. Examples of suitable catalysts are described in U.S. Pat. Nos. 8,642,498, 8,652,988, 8,735,314, 8,877,966, US2014/277384 and U.S. Pat. No. 8,765,629.

However, there are certain disadvantages associated with the use of some known catalysts, particularly vanadium-phosphorus-oxide catalysts. In particular, that they show a tendency to low selectivity of the desired acrylic acid or acrylate at low alkanoic acid to alkylenating agent ratios. This low selectivity reduces the commercial attractiveness of using low alkanoic acid to alkylenating agent ratios as some of the feedstock is lost into an unrecoverable form.

Alternative catalysts have also been investigated with a view to improving the reaction. In U.S. Pat. Nos. 8,642,498 and 8,652,989 a vanadium-titanium-phosphorous oxide is suggested while U.S. Pat. No. 8,735,314 describes a catalyst formulation comprising vanadium, titanium, ethylene glycol and citric acid. A multi-metal oxide catalyst of vanadium, phosphorous, iron with one of molybdenum, bismuth, cobalt, nickel, silicon, zinc, hafnium, zirconium, titanium, chromium, manganese, copper, boron, tin and niobium and one of lithium, potassium, sodium, rubidium, caesium and thallium is disclosed in U.S. Pat. No. 8,877,966.

It has also been suggested, such as in US2014/343318, that improved catalyst performance may be noted where the average oxidation state of vanadium within the catalyst is between +4.4 and +5.

Binary vanadium-titanium phosphate catalysts have also been studied. However, the conversion and selectivity noted in the reaction of acetic acid with formaldehyde are lower than desired. Vanadyl pyrophosphate catalysts have also been extensively studied both alone and in combination with other phosphates such as titanium pyrophosphates. While several studies have shown that vanadium-titanium-phosphorous ternary oxides may demonstrate good catalytic performance in the aldol condensation of acetic acid, with methanol and formaldehyde, $TiO_2$, $V_2O_5$—$TiO_2$, and $TiO_2$—$P_2O_5$ were not found to be as effective.

It has recently been found that vanadium-titanium-phosphorus catalysts are particularly useful for the production of unsaturated carboxylic acids such as acrylic acid. Where a vanadium-titanium-phosphorus catalyst is used, deactivation of the catalyst can be problematic. Deactivation is caused by a number of factors including carbon laydown. As the catalyst is deactivated its ability to function effectively is diminished. Since replacing the catalyst would be expensive, it is desirable to treat the catalyst such that it is regenerated.

Several methods for regenerating catalysts used in the production of unsaturated carboxylic acids have been suggested. For example, in the process described in U.S. Pat. No. 8,765,629, where inhibiting coke formation occurs on the catalyst, such as vanadium-titanium-phosphorus catalyst, a regeneration step is carried out between reaction runs. Regeneration takes place either in air or an atmosphere of 6% oxygen and 94% nitrogen at a temperature of 400° C. in the absence of water. It is indicated that it is important to avoid the presence of water since its presence will inhibit the condensation reaction.

Typically, the reactions by which unsaturated carboxylic acids are formed are carried out at below 400° C., for example at about 325° C. or less. Regenerating catalyst at a temperature that is higher than normal operation temperatures, such as at 400° C., is unfavourable as it requires additional heating to raise the temperature. Thus the reaction system needs to be modified in order to be able to withstand the higher temperature. Further, the process of cycling the temperature between the higher temperature for regeneration and the lower temperature for reaction creates a time delay in the process. This reduces the output that can be achieved within a fixed period of time. The regeneration process of U.S. Pat. No. 8,765,629 cannot simply be used at temperatures below 400° C. to address these issues as the results are inadequate.

An alternative proposal for regeneration of a catalyst is identified in US2014/0121410 in which the catalyst comprising vanadium, titanium, bismuth or tungsten, or combinations thereof is contacted with a stream comprising a regenerating agent. Various regenerating agents are suggested, including oxidants such as oxygen, ozone and nitrous oxides and reducing agents such as hydrogen. It is also suggested that the stream may include a diluent such as steam. However, no indication is provided of suitable conditions, such as temperature, for the regeneration.

In the process described in US2014/0343318 the vanadium-phosphorus oxide catalyst may be regenerated by passing a regeneration gas over the deactivated catalyst at a temperature of from 200 to 450° C. The regeneration gas comprises molecular oxygen and at least one inert gas such as nitrogen or a noble gas. A similar process is described in US2014/0343319.

Regeneration under these conditions can take a considerable period of time, even taking up to a number of days. Since the reactor is off-line for during this time, it is commercially undesirable. A further problem is that the high levels of oxygen required have substantial drawbacks from both an economic and safety viewpoint. High oxygen levels can lead to an uncontrolled exotherm in a commercial reactor, which at best will severely damage the catalyst and at worst may lead to a catastrophic loss of containment. Also, the increased amount of oxygen will also increase the risk of forming an explosive atmosphere in the reaction system.

Whilst these processes may allow some catalyst regeneration, there is still a need for an improved regeneration process which addresses, and preferably overcomes at least one of the problems detailed above.

It is therefore desirable to provide to provide a process which can regenerate catalyst, particularly catalysts used for the production of unsaturated carboxylic acids such as acrylic acid, and in particular a process which is suitable for the regeneration of vanadium-titanium-phosphorus catalysts at a temperature that is the same or similar to the temperature required for the process in which the catalyst may be used.

It has now surprisingly been found that effective regeneration of vanadium-titanium-phosphorus catalysts can be achieved without requiring a regeneration temperature significantly higher than the process temperature when the regeneration agent comprises steam.

Thus, according to a first aspect of the present invention, there is provided a process for regenerating a deactivated vanadium-titanium-phosphorous catalyst which has been used in the production of unsaturated carboxylic acid, wherein the process comprises contacting the deactivated vanadium-titanium-phosphorous catalyst with a regeneration stream comprising steam as a regeneration agent at a temperature which is the same or similar to that used in the production of the unsaturated carboxylic acid.

Without wishing to be bound by any theory it is believed that the steam present during regeneration assists in the removal of any carbon deposited on the surface of the catalyst and/or there may be some reforming of carbon organics present. This may be observed by the increase of carbon monoxide and hydrogen in a vent gas. It is also believed that the oxygen in the regeneration stream enhances the steam reforming. This may be observed by an increase in hydrogen and a decrease in organics in the vent gas.

In one arrangement, the process is for regenerating a deactivated catalyst which has been used in the production of acrylic acid. The catalyst may be any suitable vanadium-titanium-phosphorous catalyst. In one arrangement it may be a catalyst prepared according to the process set out in U.S. Pat. No. 8,765,629 the contents of which are incorporated herein by reference. However, it may be used with other vanadium-titanium-phosphorous catalysts including those prepared in accordance with the processes described in U.S. Pat. Nos. 8,889,586, 8,652,988 and 8,877,966, the contents of which are also incorporated herein by reference. Preferably the catalyst contains at least 10% by weight of titanium.

Preferably the molar ratio of vanadium to titanium in the catalyst is in the range 1:1.5 to 1:2.5. Preferably the molar ratio of vanadium to phosphorous in the catalyst is in the range 1:4.5 to 1:5.5. In one arrangement the molar ratio of vanadium to titanium to phosphorous can be in the region of about 1:2:5.

The temperature at which the process is carried out may be any suitable temperature provided that it is same or similar to the temperature at which it is used. Generally the temperature will be at or above the temperature at which the reaction is to be carried out. In one arrangement, the process is carried out at a temperature which is up to about 75° C., about 60° C., about 50° C., about 40° C., about 30° C., about 20° C., about 10° C. above or at about the temperature used in the production of the unsaturated carboxylic acid.

In one arrangement, the deactivated catalyst is contacted with the regeneration stream at a temperature of about 400° C. or less, about 380° C. or less, about 360° C. or less, or about 340° C. or less. In one arrangement, temperatures of from about 300° C. to about 350° C., from about 310° C. to about 340° C., from about 320° C. to about 330° C. or about 325° C. may offer various advantages.

Whilst the mechanism for regeneration utilising steam as the regeneration agent is not fully understood, it is clear that the conventional view that steam behaves as an inert species and can only be used as a diluent is incorrect. Rather, the steam has an active role to provide enhanced regeneration and enables the regeneration to be carried out at lower temperatures than have been able to be used previously. Without wishing to be bound by any theory it is believed that the presence of steam in the regeneration reaction not only enables the removal of various components which have been laid down on the catalyst but also helps to prevent formation of the para-formaldehyde during the condensation reaction in which the catalyst will be used.

The process of the present invention may be carried out at any suitable pressure. In one arrangement, the process may be carried out at a pressure of from about 0 kPa to about 6000 kPa. Generally it will be carried out at pressures of about 1000 kPa or below. In one arrangement, the process may be carried out in a vacuum i.e. at about 0.1 kPa. In one arrangement it may be run at pressures close to but above atmospheric pressures and thus pressures of from about 130 kPa to about 250 kPa or from about 170 kPa to about 200 kPa may be used. Preferably the process used will be the same or similar to the pressure used in the production of the unsaturated carboxylic acid.

It will be understood that the temperature used may vary with the pressure used.

Any suitable gas hourly space velocity rates (GHSV) may be used. In one arrangement, the GHSV may be from about 500 to about 10000 $Nm^3/m^3/h$. In one alternative arrangement, the GHSV may be from about 4000 to about 5000 $Nm^3/m^3/h$. Rates in the region of about 4500 $Nm^3/m^3/h$ may offer some advantages.

The regeneration stream may comprise solely the regeneration agent steam. However, generally other gases may be present such as nitrogen and/or inert gasses. This is particularly appropriate at lower temperatures.

In one arrangement, the regeneration process is carried out at not only a temperature which is the same or similar to that used in the production of the unsaturated carboxylic acid but at other similar conditions such as pressure, space velocity and the like. This enables the equipment required to cycle between a process and a regeneration unit to be minimal.

Where nitrogen is used, any suitable ratio of nitrogen to steam may be used. A mole ratio of about 1.5 to about 2.5 steam to about 1 part nitrogen may be advantageous. Mole ratios of about 1.8 to about 2.2 steam to about 1 part nitrogen, or from about 1.9 to about 2.1 parts to about 1 part nitrogen or about 2 parts steam to about 1 part nitrogen may be used.

In some embodiments, the regeneration stream may further comprise oxygen. It will be understood that the oxygen and nitrogen may be provided by any suitable source. It may be advantageous for the oxygen and nitrogen to be provided, at least partially, by air. Where air is used, it may be deoxygenated air. Preferably the regeneration stream comprises at least 3% $O_2$ on a molar basis based on the total composition of the stream. Such an oxygen level may permit the regeneration to occur in an acceptable period of time. Preferably the regeneration stream comprises not more than 21% $O_2$, preferably not more than 15% $O_2$ and more preferably not more than 10% $O_2$ (all on a molar basis based on the total composition of the stream). Such oxygen levels can be provided without needing to enrich air and may advantageously avoid explosion risk.

Figure 2:
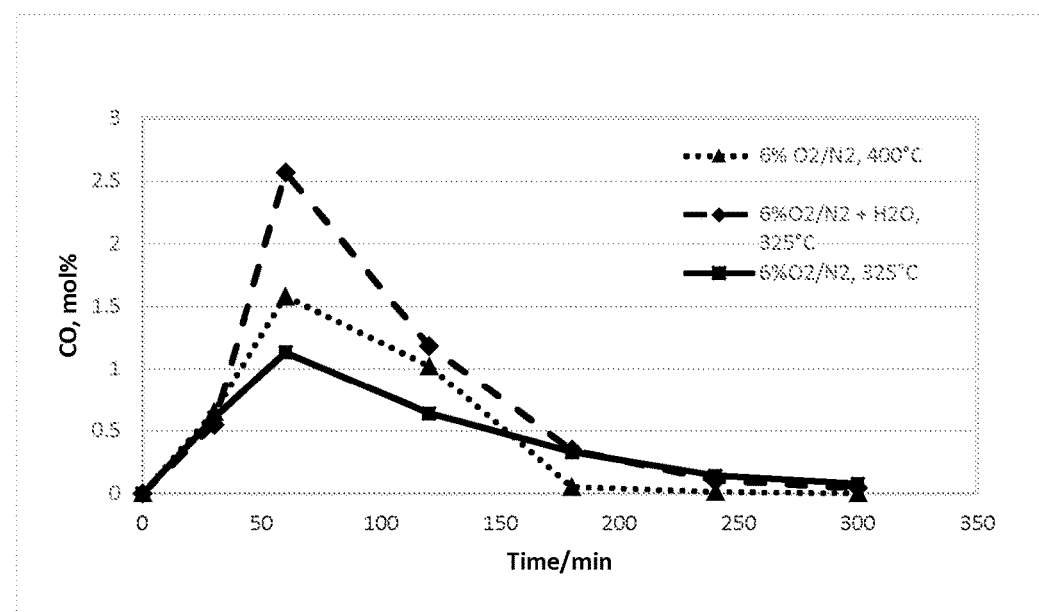
Figure 3:
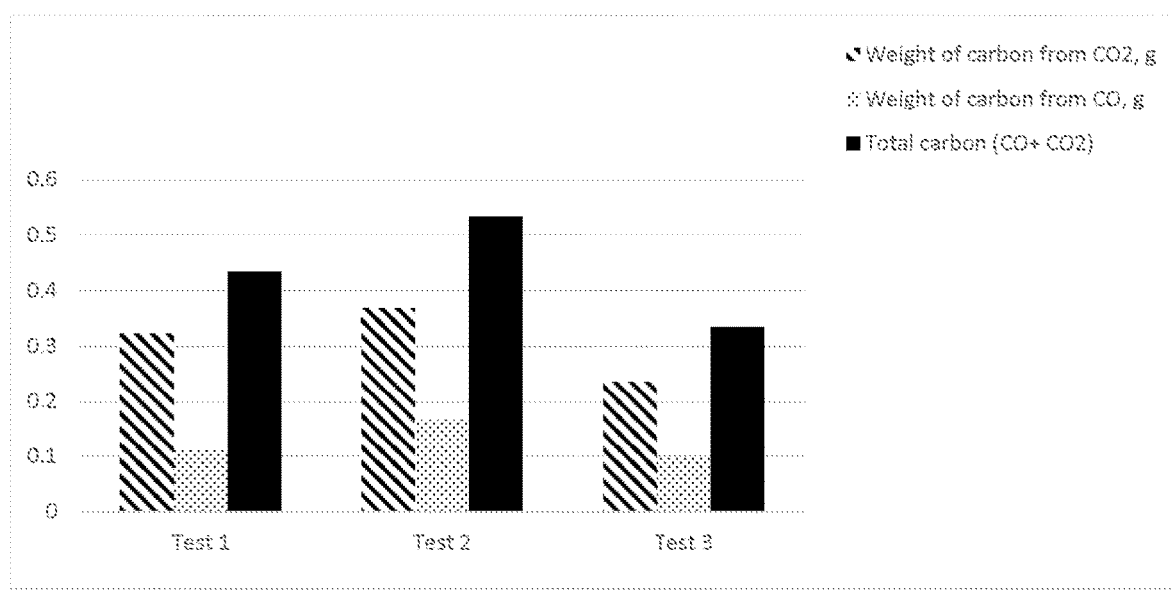

The present invention will now be described by way of example with reference to the following Example and the accompanying figures in which:

FIG. 1 is a graph illustrating the results of Example 1;
FIG. 2 is a graph of data generated from that in FIG. 1;
FIG. 3 is a graph illustrating the carbon laydown removed.

EXAMPLE 1

A feed stream comprising formaldehyde and acetic acid was passed over a vanadium-titanium-phosphorus catalyst and the catalyst allowed to deactivate. The catalyst was then regenerated by contact with a regeneration stream. The amount of $CO_2$ in the exit gas was monitored. The process was then repeated using different regeneration conditions. The conditions used for each regeneration process are outlined in Table 1.

TABLE 1

|  | Composition of Regeneration Stream | Temperature (° C.) |
|---|---|---|
| Test 1 | 6% $O_2/N_2$ (8 l/h) | 400 |
| Test 2 | 6% $O_2/N_2$ (8 l/h) + $H_2O$ (0.2 ml/min) | 325 |
| Test 3 | 6% $O_2/N_2$ (8 l/h) | 325 |

Data showing the concentration of $CO_2$ and CO in the exit gas over time for each regeneration run can be found in Table 2 and FIGS. 1 and 2.

TABLE 2

|  | Test 1 | | Test 2 | | Test 3 | |
|---|---|---|---|---|---|---|
| Time/min | $CO_2$ | CO | $CO_2$ | CO | $CO_2$ | CO |
| 0 | 0 | 0 | 0 | 0 | 0 | 0 |
| 30 | 1.98 | 0.65 | 1.32 | 0.55 | 1.31 | 0.605 |
| 60 | 4.56 | 1.58 | 4.36 | 2.57 | 2.83 | 1.13 |
| 120 | 2.83 | 1.02 | 3.14 | 1.18 | 1.67 | 0.64 |
| 180 | 0.195 | 0.051 | 1.18 | 0.347 | 0.67 | 0.33 |
| 240 | 0.068 | 0.012 | 0.29 | 0.1 | 0.28 | 0.14 |
| 300 | 0.051 | 0 | 0.082 | 0.043 | 0.205 | 0.076 |

As can be seen, the incorporation of water into the regeneration stream results in removal of $CO_2$ at 325° C. which is comparable to the removal generated by the regeneration stream consisting of 6% $O_2/N_2$ stream at 400° C. The $CO_2$ removal achieved by the 6% $O_2/N_2$ stream at 325° C. was less effective than water containing stream at the same temperature. Thus, as can be seen, the presence of water enhanced the $CO_2$ removal capabilities of the regeneration stream.

The data in Table 2 gives a total laydown carbon removed as set out in Table 3.

TABLE 3

|  | Test 1 | Test 2 | Test 3 |
|---|---|---|---|
| Weight of carbon from $CO_2$, g | 0.323 | 0.368 | 0.236 |
| Weight of carbon from CO, g | 0.111 | 0.165 | 0.098 |
| Total carbon ($CO_2$ + CO) | 0.434 | 0.533 | 0.334 |

This is represented in FIG. 3.

Thus, in this series of tests which all utilise the same catalyst, run time, reaction conditions, and feed but which are regenerated by the processes given in Table 1, it is demonstrated that with the regeneration of the present invention, more of the carbon laydown is removed at lower temperatures than is achievable with a straight oxidative regeneration (i.e. comprising oxygen only).

With steam present, some hydrogen was noted in the vent gas which suggests a reaction taking place which can be considered as equivalent to steam reforming. As the hydrogen is not equimolar with the carbon monoxide, it is postulated that there are two reaction mechanisms occurring. The details of the hydrogen noted are set out in Table 4. No organics were noted.

TABLE 4

| Tim/min | Test 1 $H_2$ | Test 2 $H_2$ | Test 3 $H_2$ |
|---|---|---|---|
| 0 | 0 | 0 | 0 |
| 30 | 0 | 0.012 | 0 |
| 60 | 0 | 0.42 | 0 |
| 120 | 0 | 0.206 | 0 |
| 180 | 0 | 0.061 | 0 |
| 240 | 0 | 0.034 | 0 |
| 300 | 0 | 0.08 | 0 |

EXAMPLE 2

The treatment of a catalyst in the presence of steam only as regeneration was carried out at 400° C. Table 5 shows that the peak carbon removal takes longer to achieve (120 minutes rather than 60 minutes when oxygen is present). There is some reaction between water and carbon that sees the formation of carbon oxides but there are also organics present in the regeneration vent gas. The overall carbon oxides to hydrogen ratio are also higher in table 5 than in test 2 of example 1, which suggests that the oxygen in test 2 of example 1 has enhanced the reforming regeneration mechanism in test 2 of example 1.

TABLE 5

| Time/min | $CO_2$ | CO | $H_2$ | $C_2H_4$ | $C_3H_6$ |
|---|---|---|---|---|---|
| 0 | 0 | 0 | 0 | 0 | 0 |
| 30 | 0.1 | 0.08 | 0.03 | 0.039 | 0.015 |
| 60 | 0.71 | 0.236 | 0.07 | 0.129 | 0.021 |

TABLE 5-continued

| Time/min | CO$_2$ | CO | H$_2$ | C$_2$H$_4$ | C$_3$H$_6$ |
|---|---|---|---|---|---|
| 120 | 1.14 | 0.57 | 0.03 | 0.017 | 0.004 |
| 180 | 0.38 | 0.23 | 0.017 | 0 | 0 |
| 240 | 0.15 | 0.075 | 0.011 | 0 | 0 |
| 300 | 0.035 | 0.011 | 0 | 0 | 0 |

The invention claimed is:

1. A process for regenerating a deactivated vanadium-titanium-phosphorous catalyst comprising vanadium, titanium, phosphorous, oxygen, and less than 30 wt % of any other metal or any metal oxide, wherein the catalyst has been used in the production of unsaturated carboxylic acid, wherein the process comprises contacting the deactivated vanadium-titanium-phosphorous catalyst with a regeneration stream comprising steam as a regeneration agent at a temperature which is the same or similar to that used in the production of the unsaturated carboxylic acid, and wherein the process is carried out at a gas hourly space velocity rate of from about 500 to about 10000 Nm$^3$/m$^3$/h.

2. The process according to claim 1 wherein the process is for regenerating a deactivated vanadium-titanium-phosphorous catalyst which has been used in the production of acrylic acid.

3. The process according to claim 1 wherein the temperature at which the process is carried out is up to about 75° C. above the temperature used in the production of the unsaturated carboxylic acid.

4. The process according to claim 1 wherein the process is carried out at a temperature of about 400° C. or less.

5. The process according to claim 1 wherein the process is carried out at a pressure of from about 0 kPa to about 6000 kPa.

6. The process according to claim 5 wherein the process is carried out in a vacuum.

7. The process according to claim 5 wherein the process is carried out at a pressure of about 130 kPa to about 250 kPa.

8. The process according to claim 1 wherein the regeneration stream additionally comprises nitrogen.

9. The process according to claim 8 wherein the mole ratio of steam to nitrogen is about 1.5 to about 2.5 steam to about 1 part nitrogen.

10. The process according to claim 1 wherein the regeneration stream further comprises oxygen.

* * * * *